United States Patent
Cohen

(10) Patent No.: US 6,689,815 B2
(45) Date of Patent: Feb. 10, 2004

(54) INTRATUMORAL USE OF DINITROCHOROBENZENE: COMPOSITION AND USE OF INJECTIONS INCLUDING PARTICULAR APPLICATIONS

(76) Inventor: Max Harry Cohen, 8812 Twin Creek Ct., Potomac, MD (US) 20854

( * ) Notice: Subject to any disclaimer, the term of this patent is extended or adjusted under 35 U.S.C. 154(b) by 210 days.

(21) Appl. No.: 09/978,286

(22) Filed: Oct. 17, 2001

(65) Prior Publication Data

US 2003/0072825 A1 Apr. 17, 2003

(51) Int. Cl.[7] .............................................. A61K 31/135
(52) U.S. Cl. ....................................................... 514/646
(58) Field of Search ......................................... 514/646

(56) References Cited

U.S. PATENT DOCUMENTS 6,350,451 B1 * 2/2002 Horn et al. ............... 424/184.1

OTHER PUBLICATIONS

Cohen et al.; Intralesional Treatment of Recurrent Metastatic Cutaneous Malignant Melanoma; Cancer 41:2456–2463, 1978.*

Lukacs et al.; Immunosurgical approach to the treatment of malignant melanoma using 2,4–dinitrochlorobenzene (DNCB); Neoplasma, 31, 4, 1984, pp 437–445.*

Budzanowaska et al.; An attempt at topical DNCB immunomodulation in advanced malignant melanoma; Tumori, 74: 519–522, 1988.*

* cited by examiner

*Primary Examiner*—Jerome D. Goldberg

(57) ABSTRACT

Dinitrohalogenated compounds may be utilized by injection in certain clinical situations to provide a possibility of long term control of human malignancy. In some of those settings no other treatment offers such potential. Preparation methods may include acetone, olive oil, microsomes, liposomes, or combinations thereof. Optimum pretreatment management, dosing and injection techniques are described.

The unique aspects of the claims included herein include the methods of preparation of the chemical, the technique of injection, the dosage of each injection, and the range of potential tumor histologies. These techniques have resulted for example in successful treatment of locally metastatic scalp melanoma, the treatment for which had previously been uniformly unsuccessful. This example is particularly significant since this is one example of a site that is not otherwise amenable to successful treatment when affected by multiple progressive metastatic nodules. This condition was untreatable for cure by any other previous method, including surgery.

9 Claims, 1 Drawing Sheet

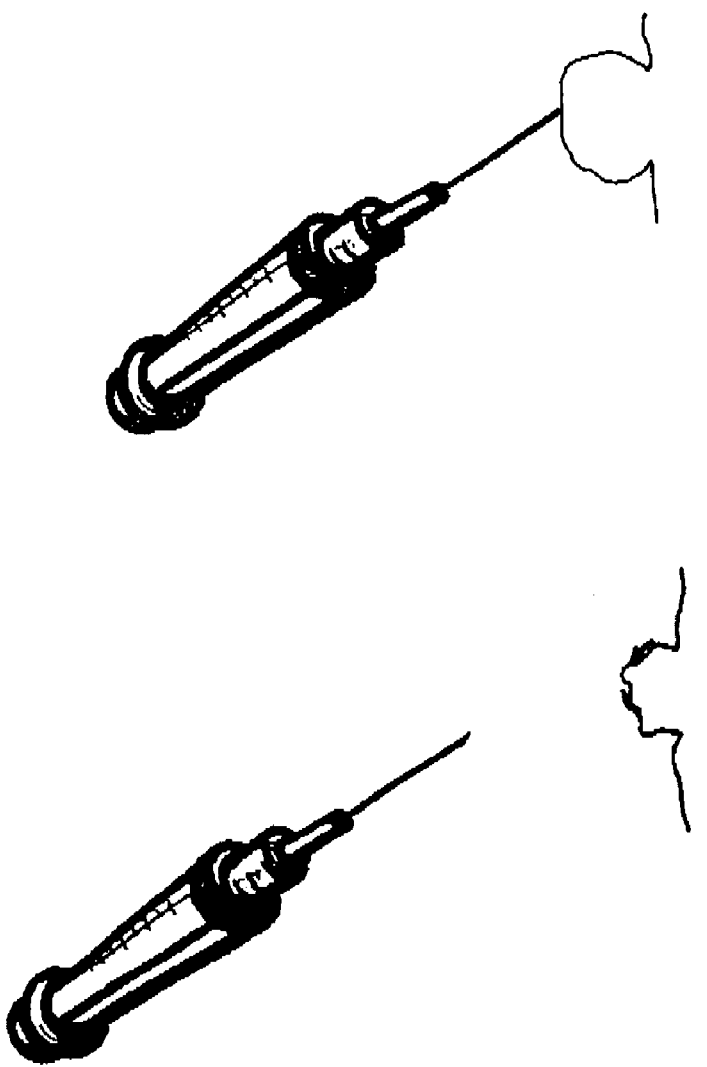

INTRATUMORAL USE OF DINITROCHOROBENZENE: COMPOSITION AND USE OF INJECTIONS INCLUDING PARTICULAR APPLICATIONS

BACKGROUND OF THE INVENTION

This invention pertains to the treatment of benign and malignant tumors by injections. Dinitrochlorobenzene (or DNCB) and other dinitrohalogenated compounds are chemicals which, when applied to the skin, act as a haptens with associated skin proteins and elicit immunological responses in individuals with intact immune systems.

DNCB has, in the past, been topically applied to the surface of the skin to areas of actinic damage, or to the surface of some human tumors, primarily superficial skin tumors such as basal cell carcinomas. The current application describes the use of the chemical as an agent for injection, and describes techniques and dosages that optimize its use as an anti-cancer agent against more aggressive malignancies.

Human tumors, benign and malignant, share most of their antigens with the antigens of normal tissues. The antigenicity of a human tumor in its human host is therefore generally low because of the relatively weak antigenic differences between tumors and normal tissues. As a result, tumors frequently become progressive, to the point where the advancing nature of the malignancy threatens the life of the affected individual.

Methodologies which increase the antigenicity of the offending tumor cells, can potentially render the cells susceptible to immunologic destruction by the host. Additionally, a tumor destructive technique that damages or weakens tumor cells may render such cells susceptible to elimination by the host.

Years ago I found that on putting certain chemicals on or into the skin that some immunological changes and other effects were seen. I did not describe how the injections were prepared, or what an ideal injection would contain. I did not describe nor did I know at that time the locations in the body that were uniquely suitable for such an approach. I did not describe the range of conditions for which the approach is applicable. I did not describe the special methodology of the injection process. Described in this application for the first time is the ideal dosing schedule. Effective methodology is described herein for treating sites not previously successfully treated. The combination of DNCB or dinitrofluorobenzene (DNFB) with other products and delivery systems is described, as well.

Malignant melanoma is a cancer that spreads locally through "skip metastases," or nests of tumor in the skin separated by histologically normal tissue from the site of the primary or original malignancy. As these nests of tumor cells enlarge to a noticeable size they release other cells that form another series of tumor nodules which again may be separated by intervening normal tissues from the originating nodules of malignancy. During such a progression it becomes rapidly apparent that surgical removals are inadequate to control the disease because of microscopic tumor deposits present at a considerable distance from the visible tumor recurrences. The tumors are notoriously resistant to chemotherapy or radiation therapy, the two other mainstays of cancer treatment, besides surgery. It is therefore of particular significance for this subset of patients that the techniques described herein are capable of delaying tumor progression, and in some cases by providing long term survival free of malignancy in a setting where the likelihood of the patient succumbing to the malignancy is otherwise essentially 100%.

BRIEF SUMMARY OF THE INVENTION

There are certain conditions in human cancer care where there has previously been no treatment capable of producing long term cancer control. Malignant melanoma, for example spreads as widely as any human cancer. As it continues to spread locally in the surrounding skin, it becomes unstoppable by repeated surgical excisions. The prognosis for survival at this point drops essentially to zero percent. If the recurrences are in an extremity, such as the leg, the option exists of using heated chemotherapy pumped into the blood vessels of the leg. The procedure is labor intensive, costly and difficult to repeat when the cancer nodules begin to recur. If the melanoma recurs and the nodules of recurrences are on the scalp, there is currently no effective treatment available to patients whose nodules continue to recur. In the case of recurrent scalp melanoma, systemic chemotherapy cannot be delivered into blood vessels running to the scalp, since the brain would be damaged as a side effect. Using methods to be described, DNCB and perhaps other dinitrohalogenated benzene compounds, can arrest and reverse such growth in some patients, on a long term basis, in cases where no other treatment option can control the disease. Details of the preparation method are described. An optimal immunization or preutilization schedule is described. Optimal dosage and techniques of injection are described. Methods of delivery of DNCB and combinations with other techniques are described. Comparison with the prior art is discussed, together with mention of improvements in methodology.

DETAILED DESCRIPTION OF THE INVENTION

Due to the irritating properties of the drug mask and examining gloves were worn during the entire procedure of preparing the injectable material due to the irritating properties of the drug.

The DNCB was weighed directly into an appropriate volumetric flask. This eliminates the possibility of spillage on transfer. The weighing was done on the Sartorius balance. Acetone in a volume of 1 ml. per 20,000 mcgm of DNCB was used to bring this flask up to volume and the solution was mixed well. While the solution was being realized, a 10 ml. glass syringe was fitted with a metal hub needle. (NOTE: DO NOT USE PLASTIC). Small amounts (6–8 ml.) of the DNCB solution were transferred to a small beaker and drawn up into the glass syringe. The solution was then transferred to 2 ml. vials. The vials were then closed with special Teflon seals.

A spectrophotometric (ultraviolet) method of assay suitable for intact 2, 4 dinitrochlorobenzene was used. Several samples were taken and each was evaporated to dryness and then diluted with absolute ethanol to a concentration of about 1 ml./100 ml. The compound's absorbance was then measured at 238 millimicrons on a Cary Model 11 Recording Spectrophotometer. An acetone solution of this material was found to be at full potency and purity after one year at 0 degrees C.

I have also used dinitrofluorobenzene for human intratumoral injections, and either of the above mentioned dinitrohalogenated compounds may also be dissolved in olive oil to prepare a suitable preparation for intratumoral injection.

Technique of injection: Three cc of ½% lidocaine (with epinephrine 1:100,000) is injected superficially into the tumor nodule. This injection is unlike the standard anesthetic injections around a tumor nodule, which focuses on the areas to be subjected to scalpel excision. Rather the injection is done more centrally to try to open up intradermal and other spaces to accommodate the subsequent anti-tumor injection, and to afford optimal pain relief for the subsequent injection. It is important to then inject the DNCB solution superficially so that it permeates the superficially located intradermal nodule. Under the ideal circumstances the tumor nodule expands or enlarges during this "expanding injection." (see FIG. 1). The nodule and surrounding tissue ideally assumes a slightly yellowish to orange hue during the day or so following injection. The ideal concentration of DNCB in acetone is 2000 micrograms per 0.1 cc of acetone.

Sites on the scalp have no other effective method of treatment. However, they respond well to this methodology. Breast cancer recurrences on the chest wall may be treated by this technique, as well as any tumor, locally recurrent, not amenable to control by surgical resections. I have not publically disclosed the information in the section, and believe it to be necessary to the obtaining of useful results. Utilizing the technique of superficial injection of 2000 microgram of DNCB has recently yielded successful results with long term survival, in the treatment of metastatic scalp melanoma. In earlier attempts, using different techniques, the patients did not experience such survival.

We propose that microsomal and liposomal vehicles be utilized with dinitrochlorobenzene and dinitrofluorobenzene. Dinitrochlorobenzene or other dinitrofluorinated benzene injections combine well with technologies designed to increase tumor antigenicity. Allovectin® for example relies on the use of naked DNA to enhance reactivity to the major histocompatibility complex which in turn assists with antigen presentation to the immune system and presumed increased antitumor activity. The use of other dinitrohalogenated benzenes to increase the antigenicity of the tumor nodules should enhance the efficacy of the antitumor reactivity.

The hapten effect of dinitrohalogenated benzene compounds can be utilized to enhance the effectiveness of genetic mechanisms enhancing antitumor activity.

What I claim as my inventions are:

1. A method of treating repeatedly recurrent malignant tumor nodules in the skin of a subject comprising injecting approximately 0.1 cc of a solution of a dinitrohalogenated benzene compound into the malignant nodule wherein said compound is injected without prior sensitization using an expanded injection.

2. The method of claim 1 wherein said dinitrohalogenated compound is dinitrochlorobenzene, in a concentration of approximately 2000 micrograms in 0.1 cc of acetone.

3. The method of claim 2 wherein said locally recurrent tumor is melanoma, breast cancer or squamous cancer.

4. The method of claim 1 wherein the locally recurrent tumor is located on the scalp.

5. The method of claim 1 wherein the dinitrohalogenated compound is dinitrofluorobenzene in 0.1 cc of acetone-olive oil.

6. The method of claim 5 wherein the recurrent tumor nodule or nodules are melanoma, breast cancer, or squamous cancer metastatic in the skin.

7. The method of claim 5 wherein the locally recurrent tumor is located on the scalp.

8. The methods of claim 3, 4, 6 or 7 wherein the dinitrochlorobenzene and dinitrofluorobenzene are injected together at the same time.

9. The method of claim 3, 4, 6, 7 or 8 wherein the tumor nodule is distantly rather than locally metastatic.

* * * * *